US012064329B2

(12) United States Patent
Allen et al.

(10) Patent No.: US 12,064,329 B2
(45) Date of Patent: Aug. 20, 2024

(54) SURGICAL IMPLANT SYSTEM AND METHOD

(71) Applicant: Boston Scientific Scimed, Inc., Maple Grove, MN (US)

(72) Inventors: John J. Allen, Mendota Heights, MN (US); Andreas C. Pfahnl, Eden Prairie, MN (US); Jason R. Gerold, Shakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 228 days.

(21) Appl. No.: 14/777,496

(22) PCT Filed: Mar. 17, 2014

(86) PCT No.: PCT/US2014/030894
§ 371 (c)(1),
(2) Date: Sep. 15, 2015

(87) PCT Pub. No.: WO2014/146023
PCT Pub. Date: Sep. 18, 2014

(65) Prior Publication Data
US 2016/0038267 A1 Feb. 11, 2016

Related U.S. Application Data

(60) Provisional application No. 61/786,361, filed on Mar. 15, 2013, provisional application No. 61/792,142, filed on Mar. 15, 2013.

(51) Int. Cl.
*A61F 2/00* (2006.01)
*A61B 17/04* (2006.01)
(Continued)

(52) U.S. Cl.
CPC ........ *A61F 2/0004* (2013.01); *A61B 17/0401* (2013.01); *A61B 2017/00477* (2013.01);
(Continued)

(58) Field of Classification Search
CPC ...... A61B 17/0401; A61B 2017/00477; A61B 2017/00805; A61B 2017/0403;
(Continued)

(56) References Cited

U.S. PATENT DOCUMENTS 3,762,418 A * 10/1973 Wasson ............ A61B 17/06004
606/226
2004/0002734 A1 * 1/2004 Fallin ................. A61B 17/0401
606/232
(Continued)

FOREIGN PATENT DOCUMENTS

WO 2013016306 A1 1/2013
WO 2014190080 A1 11/2014

OTHER PUBLICATIONS

First Examination Report for Australian Application No. 2019201115, mailed Dec. 19, 2019, 3 pages.
(Continued)

*Primary Examiner* — Darwin P Erezo
*Assistant Examiner* — Christina C Lauer
(74) *Attorney, Agent, or Firm* — Brake Hughes Bellermann LLP

(57) ABSTRACT

An implant and suture locking system is provided. The implant can include a lateral or distal anchor, and a medial or proximal anchor. One or more suture loops can extend between and operatively connect the anchors. A medial suture loop can extend through apertures in the medial anchor to provide efficient and easily adjustable tensioning and suture locking for the implant.

20 Claims, 18 Drawing Sheets

(51) Int. Cl.
   *A61B 17/00* (2006.01)
   *A61B 17/06* (2006.01)
   *A61B 90/92* (2016.01)

(52) U.S. Cl.
   CPC ............... *A61B 2017/00805* (2013.01); *A61B 2017/0403* (2013.01); *A61B 2017/0409* (2013.01); *A61B 2017/0412* (2013.01); *A61B 2017/0414* (2013.01); *A61B 2017/0417* (2013.01); *A61B 2017/0427* (2013.01); *A61B 2017/0459* (2013.01); *A61B 2017/0461* (2013.01); *A61B 2017/0464* (2013.01); *A61B 2017/0496* (2013.01); *A61B 2017/0608* (2013.01); *A61B 2017/0619* (2013.01); *A61B 90/92* (2016.02); *A61F 2/0045* (2013.01)

(58) Field of Classification Search
   CPC .... A61B 2017/0409; A61B 2017/0412; A61B 2017/0414; A61B 2017/0417; A61B 2017/0427; A61B 2017/0459; A61B 2017/0461; A61B 2017/0464; A61B 2017/0496; A61B 2017/0608; A61B 2017/0619; A61B 90/92; A61B 2017/0419; A61F 2/0004; A61F 2/0045
   USPC ......................................................... 606/232
   See application file for complete search history.

(56) References Cited

U.S. PATENT DOCUMENTS

| | | | |
|---|---|---|---|
| 2005/0033363 A1 | 2/2005 | Bojarski et al. | |
| 2006/0089525 A1* | 4/2006 | Mamo ................ | A61B 17/0401 600/37 |
| 2007/0167676 A1* | 7/2007 | Miyamoto .......... | A61B 17/3478 600/105 |
| 2009/0306711 A1* | 12/2009 | Stone ................. | A61B 17/0401 606/232 |
| 2009/0318961 A1 | 12/2009 | Stone et al. | |
| 2010/0292792 A1 | 11/2010 | Stone et al. | |
| 2011/0022061 A1* | 1/2011 | Orphanos .......... | A61B 17/0401 606/139 |
| 2012/0123474 A1* | 5/2012 | Zajac ................. | A61B 17/0401 606/232 |
| 2013/0023724 A1* | 1/2013 | Allen ................. | A61B 17/3468 600/30 |

OTHER PUBLICATIONS

Communication pursuant to Article 94(3) EPC for European Application No. 14763677.3, mailed May 10, 2021, 4 pages.

\* cited by examiner

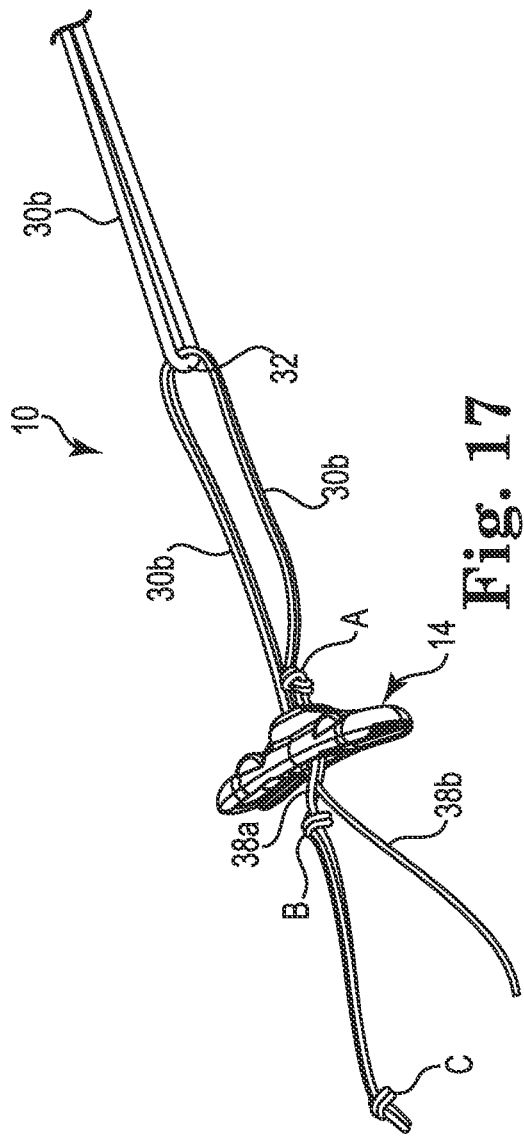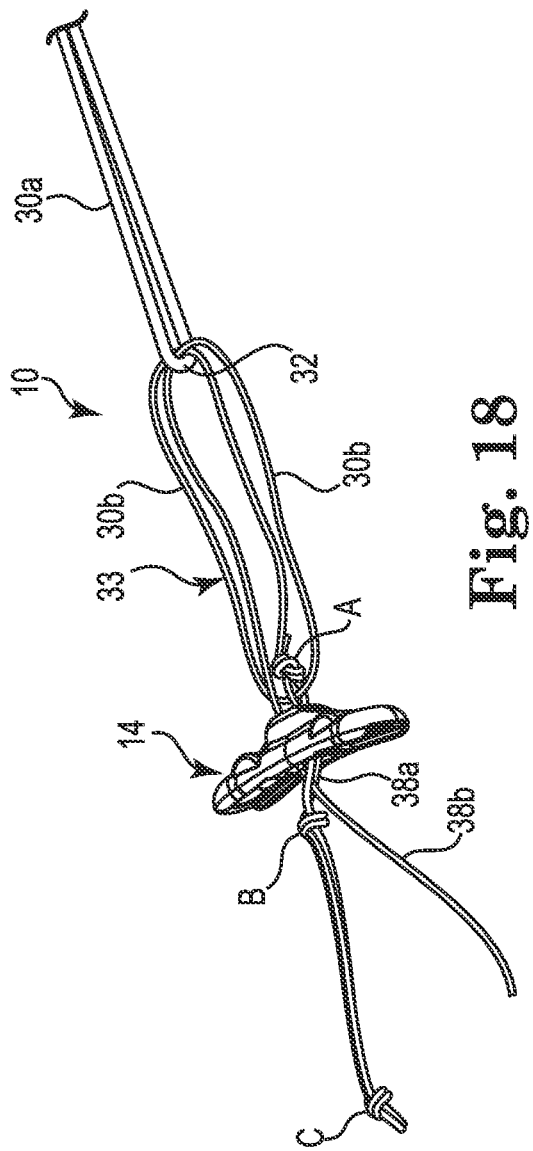

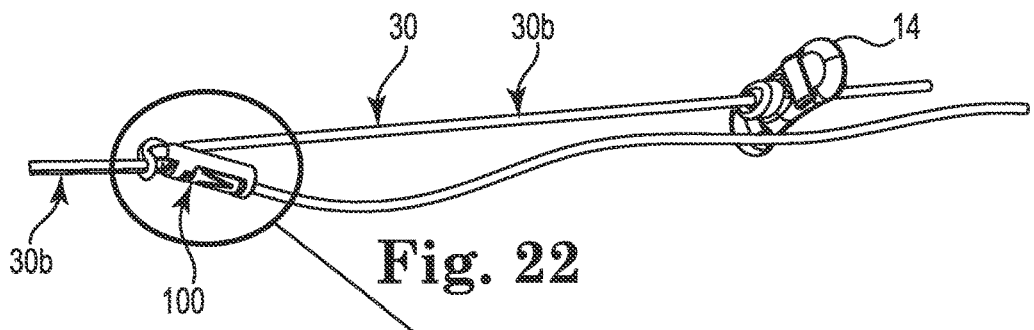
Fig. 22
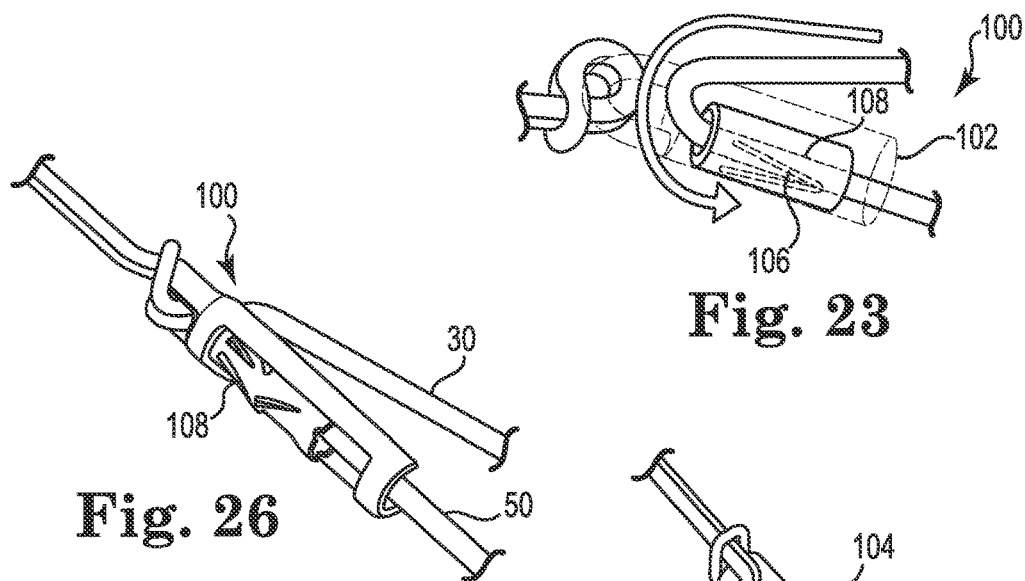
Fig. 23
Fig. 26
Fig. 25
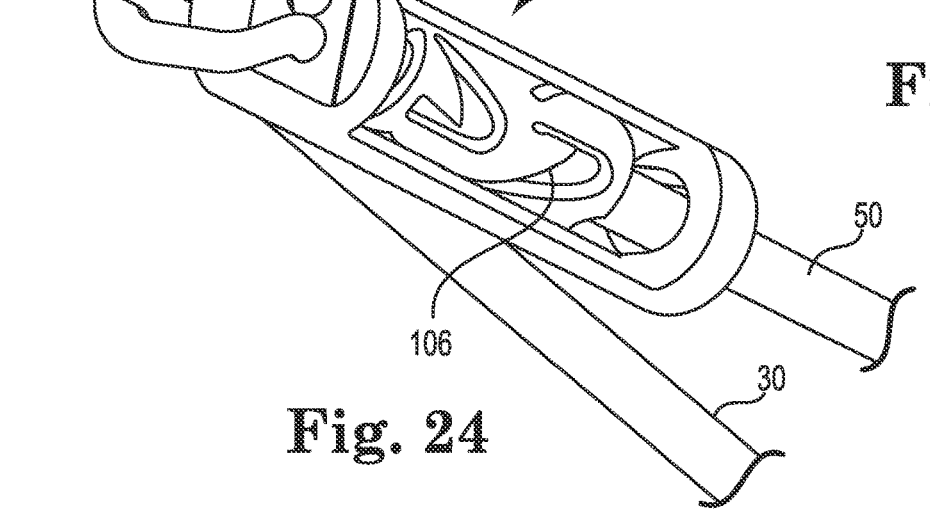
Fig. 24

SURGICAL IMPLANT SYSTEM AND METHOD

This application claims priority to and the benefit of U.S. Provisional Patent Application No. 61/792,142, filed Mar. 15, 2013, and U.S. Provisional Patent Application No. 61/786,361, filed Mar. 15, 2013, all of which are hereby incorporated fully herein by reference in their entirety.

FIELD OF THE INVENTION

The present invention relates to apparatus, tools and methods for treating pelvic conditions and, more particularly, systems and methods to support pelvic tissue by acting on, stabilizing, positioning or controlling the position of the perineal membrane or like anatomical structures.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. The urethra is the tube that passes urine from the bladder out of the body. The narrow, internal opening of the urethra within the bladder is the bladder neck. In this region, the bladder's bundled muscular fibers transition into a sphincteric striated muscle called the internal sphincter. The rectum is the most distal portion of the gastrointestinal tract. The exterior opening of the rectum is the anus. Fecal continence is related to control of the exterior sphincter and interior sphincter of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "overactive bladder," "frequency/urgency syndrome," or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. Mid-urethral slings have been effective. One type of procedure, found to be an especially successful treatment option for SUI in both men and women, is a suburethral sling procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension structures or sutures to a point of attachment (e.g., tissue or bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534, 6,110,101, 6,911,003, 6,652,450, and International PCT Publication No. 2008/057261, all of which are herein incorporated by reference in their entirety.

Fecal incontinence, like urinary incontinence, has proven to be challenging to treat. Patients whose fecal incontinence is caused by external anal sphincter injury are treated surgically, as with a sphincteroplasty. Other patients, though, are considered to have neurogenic or idiopathic fecal incontinence, and efforts to treat these patients have been less successful. These various procedures, such as postanal repair, total pelvic floor repair, muscle transposition techniques, dynamic graciloplasty, artificial sphincter procedures, and sacral nerve stimulation. Success has been limited, and the various treatment modalities can result in morbidity.

There is a desire for a minimally invasive yet highly effective treatment modality that can be used with minimal to no side effects for the treatment of both urinary and fecal incontinence. Such a modality should reduce the complexity of a treatment procedure, be biocompatible, should reduce pain, operative risks, infections and post operative hospital stays, and have a good duration of activity. Further, the method of treatment should also improve the quality of life for patients.

SUMMARY OF THE INVENTION

The present invention can include surgical instruments, implantable articles, and methods for urological applications, particularly for the treatment of stress and/or urge urinary incontinence, fecal incontinence, and prolapse by implanting a paraurethral constraining device. The constraining device or implant can control and eliminate rotational descent of the midurethra that is associated with incontinence.

Embodiments of the present invention can include apparatus and methods for treating urinary incontinence, fecal incontinence, and other pelvic defects or dysfunctions, in both males and females using one or more implants to reinforce the supportive tissue of the urethra. The implants are configured to engage and pull (e.g., pull up), restrain or reposition the supportive tissue, such as the perineal membrane, during a stress event such as coughing. The perineal membrane is the fibrous membrane in the perineum that intersects the urethra and vagina near the midurethra location and can thus be stabilized or controlled in a manner that helps restore continence. As such, systems, methods and implants can be utilized to eliminate the need for mesh or other supportive structures under the urethra that are common with other incontinence slings. The implants can be shaped to facilitate such support, e.g., provided with anchoring end portions, barbs or other devices of many available shapes and configurations. One or more anchors or tissue engagement portions can be employed to attach and stabilize the implants or devices to tissue.

Embodiments of the present invention can provide smaller implants or devices, fewer implant or device components, thus reducing the size and number of incisions, improving implant manipulation and adjustment, the complexity of the insertion and deployment steps, and healing times.

The implants can limit or resist movement of tissue such as, for example, forward rotational movement of the urethra or surrounding tissue. The present implant embodiments can utilize a perineal incision or puncture and a paraurethral constraining device. Alternatively, the device may be implanted transvaginally.

In certain embodiments, one or more paraurethral support devices are provided. Paraurethral suspension elements are provided for the treatment of SUI and other disorders. The support, extension or suspension elements can apply mechanical traction to the urethra in a manner similar to a mini-sling device, wherein tension is applied at the midurethral position to restrain that anatomical structure during stress events, such as coughing or physical activity.

An anchoring element or portion, such as a medial or proximal anchor, can be fixed on each side of the urethra on the inferior side of a tissue layer that is known to have relatively high strength and toughness. Such anatomical structures can include the uterovaginal fascia, endopelvic fascia, perineal membrane or other anatomical features at which connective support of the urethra can be established.

Embodiments of the medial anchor can be generally elongate and can extend out generally transverse from the connected suture loop. The medial anchor can include top side and bottom side surface, one or more first through-apertures, and one or more second through-apertures. Further, one or more additional apertures can be provided with the medial anchor to facilitate further attachment, and/or to provide openings to promote tissue in-growth. A lateral suture loop can connect to and extend from the lateral anchors and a medial suture loop connects with the lateral loop and extends through the medial anchor to provide efficient tensioning and locking adjustment of the implant in position after deployment.

A second anchor device, such as a distal/lateral anchor or engagement device, is placed in a lateral or superior position such that a connection between the medial and lateral anchors (via a suture, mesh, wire or like connection) can provide tensile support for the urethra during stress events. The distal anchor device can be fixated to, or around, the tendinous arch of the levator ani (white line), the Cooper's ligament, the obturator membrane, obturator internus, obturator externus, abdominal fascia, sacrospinous ligament, prepubic fascia or muscle, the pubic symphysis cartilage, or other stable anatomical structures. The distal anchor devices can be an elongate toggle anchor. In other embodiments, the anchor can include a body portion, a beveled tip, one or more expandable barbs, a thru-aperture, and an opposing end. The suture or like extension member is adapted to string or thread through the respective apertures of a series or array of such anchors. The array of anchors can be inserted within and along the interior lumen of a needle, cannula or like inserter or delivery tool for deployment. In addition, the distal anchor, or anchor array, can be directed down below the urethra for fixation, to provide an alternate control over the position and rotation of the urethra.

The final position of the implanted device creates a support structure that can include a generally straight, suspension orientation. The medial anchor can spread to better distribute the tension load over a larger surface compared to a thin suture cutting edge surface. This, in turn, promotes stability of the anchor and connecting suture and, ultimately, the target support tissue.

Various procedural steps or methods can be implemented to deploy and anchor the implant of the present invention. In one embodiment, the distal anchor is implanted, a needle is withdrawn, a free suture or connector end is delivered through the insertion opening, the second medial anchor is delivered and implanted, and the connecting suture is properly tensioned between the anchors to provide proper support. The suture or other support extensions members can be constructed to be generally flexible, or to have limited elasticity—e.g., bungee-type attributes.

Further, embodiments of the devices and their corresponding anchors, suture loops, suture locks and/or tensioning mechanisms and techniques can be employed in a myriad of surgical procedures, including orthopedic, plastic surgery, cardiovascular, and like procedures to replace or supplement any traditional or other suture tightening and tensioning techniques. The devices and methods of the present invention can significantly reduce the time of surgical procedures by allowing for fast and efficient tensioning and locking securement of the implant without requiring a physician to tie sutures or introduce additional tensioning mechanisms.

BRIEF DESCRIPTION OF THE DRAWINGS

FIGS. 15-18 show implant devices having various suture loop and/or suture configurations, in accordance with embodiments of the present invention

FIGS. 22-26 show various anchor and pulley tensioning configurations for an implant device, in accordance with embodiments of the present invention.

DETAILED DESCRIPTION OF PREFERRED EMBODIMENTS

Figure 1:
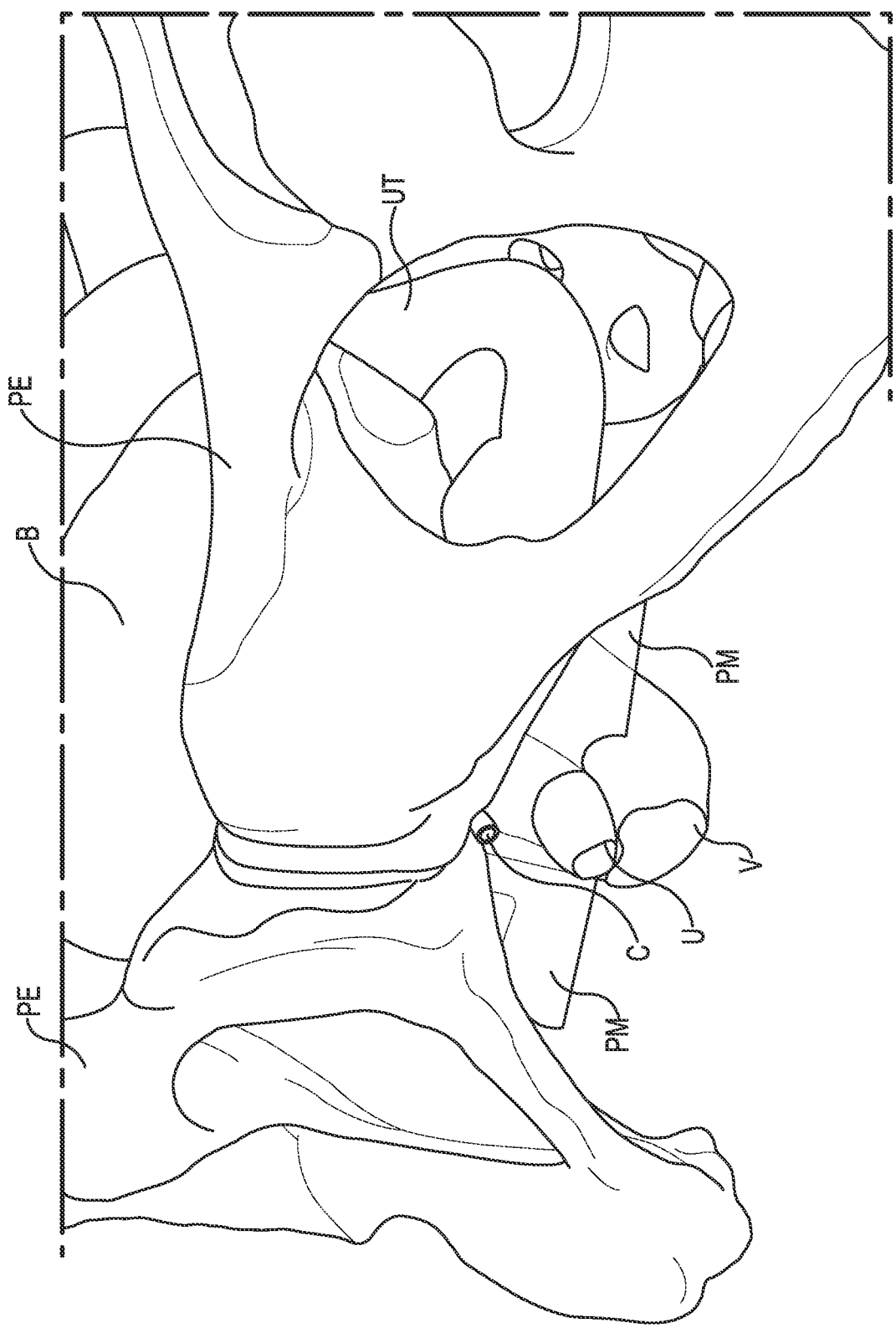
FIG. 1 is a schematic view of various anatomical structures of the female pelvic region, including urinary and reproductive systems.

FIG. 1 shows a schematic view of relevant portions of the female pelvic region, and the urinary and reproductive system, including the pelvis PE, vagina V, uterus UT, urethra U, bladder B and the deep clitoral vein C. Further, a portion of the perineal membrane PM is shown at the midurethra/distal location, providing a viable paraurethral target for stabilizing or controlling the position and movement of the urethra to assist in restoring continence.

Embodiments of the present invention can include apparatus and methods for treating urinary incontinence, fecal incontinence, and other pelvic defects or dysfunctions, in both males and females using one or more lateral implants to reinforce the supportive tissue of the urethra. One or more implant devices 10 are configured to engage and pull (e.g., pull up) or reposition support tissue (e.g., paraurethral), such as the perineal membrane, uterovaginal fascia, endopelvic fascia, or other anatomical features at which connective support of the urethra can be established. The perineal membrane intersects the urethra and vagina at the midurethra/distal location and can thus be stabilized or controlled in a manner that helps restore continence. As such, the implants 10 can be utilized to eliminate the need for mesh or other supportive structures under the urethra that is common with other incontinence slings. The implants can be shaped to facilitate such support, e.g., provided with anchoring end portions 12, barbs or other devices of many available shapes, sizes and configurations, and one or more extension members 30. The one or more extension members 30 extend between one or more medial, or proximal, anchors 14 and one or more lateral, or distal, anchors 16.

Further, embodiments of the devices 10 and their corresponding anchors, suture loops, suture locks and/or tensioning mechanisms and techniques can be employed in a myriad of surgical procedures, including orthopedic, plastic surgery, cardiovascular, and like procedures to replace or supplement any traditional or other suture tightening and tensioning techniques. The devices and methods of the present invention can significantly reduce the time of surgical procedures by allowing for fast and efficient tensioning and locking securement of the implant without requiring a physician to tie sutures or introduce additional tensioning mechanisms.

Various embodiments of the extension members 30 (e.g., 30*a*, 30*b*) can be constructed of a suture, a thin flat member, braided fibers, braided nano-fibers, an elongate mesh and other various materials and constructs. For those embodiments including braided nano-fibers, the extension member 30 can enhance and draw more collagen-producing cells to the material to promote tissue ingrown and healing.

The extension member 30 of certain embodiments of the present invention can be constructed to be generally flexible, or can have limited elasticity—e.g., bungee type attributes. For instance, the member 30 extending between the anchors 14 and anchors 16 can be an elongate member constructed of an elastomeric material having desirable tensile properties. As such, the member 30 can be stretched out for deployment and then released to provide desirable taut tension. The travel or stretching/rebound characteristics of the member 30 can vary depending on the particular elastomeric materials used in its construction. The extension member 30, such as a suture, can further include various extending tines or barbs to facilitate the tissue traction and grabbing during and after deployment.

The one or more opposing anchors 14, 16 or tissue engagement portions can be employed to attach and stabilize the implants to the tissue, as well as provide selective adjustment. The anchors or engagement portions can be configured to engage soft tissue and can include various barbs, tines, serrated edges, extending fibers, or other similar structural feature to promote tissue fixation. The anchors can be implanted in a direction lateral or adjacent from the urethra. The anchors can generally be small enough to be unnoticeable by both the patient and the patient's sexual partner. The anchors and other devices and components of the system 10 may be constructed from various biocompatible materials, such as known polymers and metals that promote long-term resilience, or other materials known to those skilled in the art.

In various embodiments, the one or more implants 10 can be placed in strategically located positions to pull up or otherwise tighten tissue and/or muscle. For instance, with certain embodiments, the tissue can be lateral or otherwise intersecting or attached (directly or indirectly) with the urethra to generally stabilize the anatomical structure of the patient. Various systems, devices, structures, techniques and methods, alone or in combination, as disclosed in U.S. Patent Publication Nos. 7,500,945, 7,407,480, 7,351,197, 7,347,812, 7,303,525, 7,025,063, 6,911,003, 6,691,711, 6,648,921, 6,612,977, 6,802,807, 2002/0161382, 2002/0147382, 2002/151762, 2004/0039453, 2008/0057261, 2008/0045782, 2010/0105979, 2011/0144417, and 2011/0201876, pending U.S. Patent Application No. 13/556,167, and International PCT Publication Nos. WO 2008/057261 and WO 2007/097994, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

Figure 2A:
FIGS. 2a-3 are schematic views of various anatomical structures of the female pelvic region, and bilateral implants having medial and lateral/distal anchors, in accordance with embodiments of the present invention.
Figure 2B:
Figure 3:
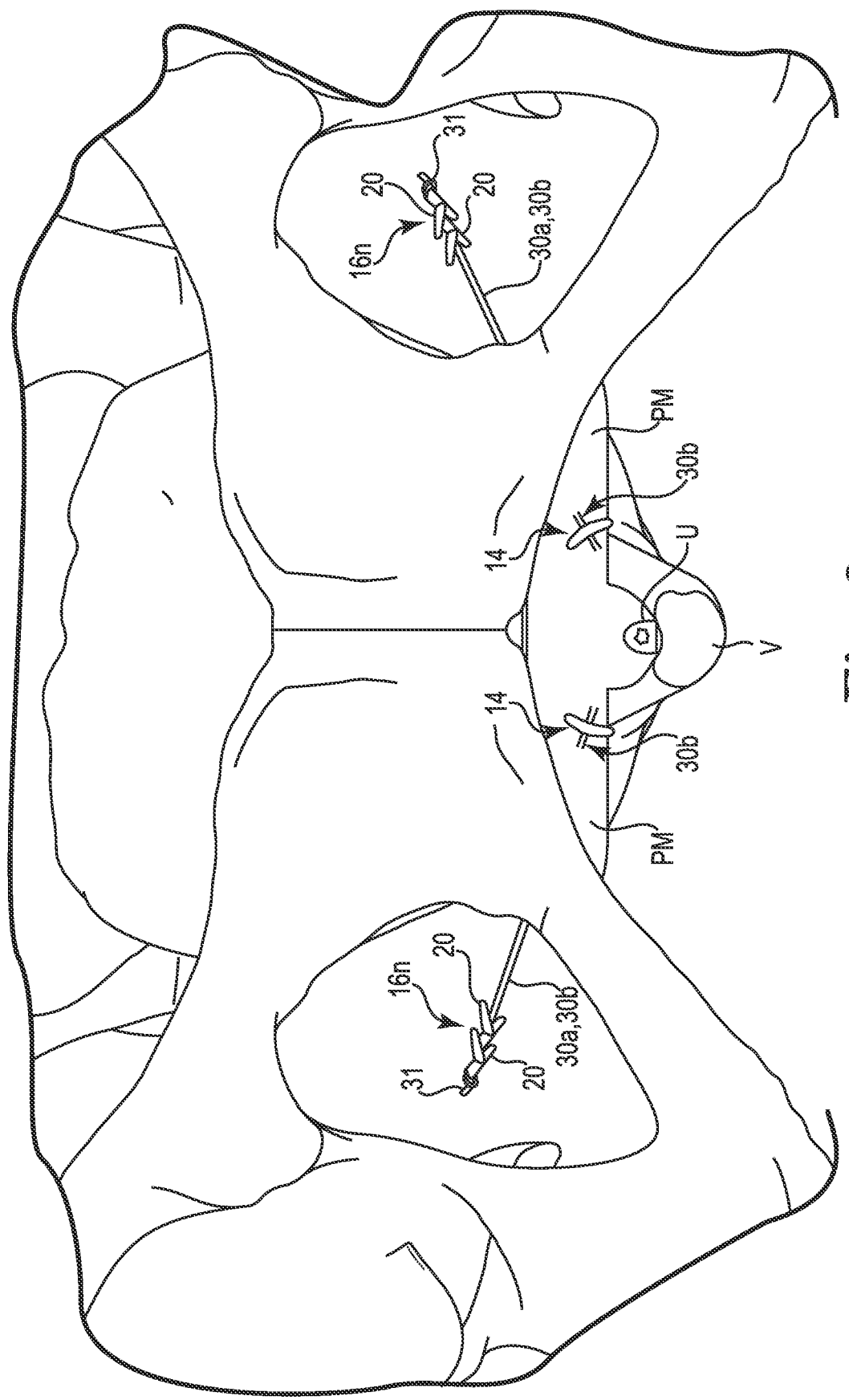

Referring generally to FIGS. 2a-3, various embodiments are shown of the tissue constraining or positioning implant system 10 having one or more attachment points in one or more membranes or other target tissue locations. Embodiments can function to restrict, limit or control movement of the mid or distal urethra, or surrounding tissue. Further, embodiments can assist in resisting forward rotational movement of the urethra or surrounding tissue, and can provide support and tension during events, such as coughing or physical activity. Various advantages of the implant 10 embodiments depicted herein include, frontal access and simpler anatomy to address, less vascularity and bleeding, reduced risk of creating retention and de novo urge, and the ability to test for continence before surgery. Additionally, the implants 10 act to oppose rotational descent of the urethra, thereby eliminating or lessening the effects of stress urinary incontinence.

Certain of the devices 12, e.g., the lateral or distal anchor 16, can be generally provided as a toggle device or in a back-to-back serial configuration, with the suture or like extension member 30 extending to provide adjustable support between the anchor devices 12. As shown in FIGS. 4-18, the anchor devices 12 can include one or more first medial or proximal anchor devices 14, and one or more second lateral or distal anchor devices 16.

Referring generally to FIGS. 4-7, the one or more medial anchors 14 is generally elongate and can extend out generally transverse from the connected suture loop 30b. The anchor 14 can include a top side or surface 14a, a bottom side or surface 14b, one or more first through-apertures 15a, and one or more second through-apertures 15b. The through-apertures 15a, 15b can be provided generally central to the medial anchor 14 and can be included within a cavity or pocket 17. A domed portion 23, or other like construct, can extend out from the top surface 14b, and can include the through-apertures 15a, 15b and/or the pocket 17. The pocket 17 can be sized and shaped to partially or completely contain the knot B when the medial loop 30b is tensioned. In addition, the pocket 17 can serve to conceal the knot B such that it causes less irritation after implantation. Further, one or more additional apertures 21 can be provided with the medial anchor 14 to facilitate further attachment, and/or to provide openings to promote tissue in-growth.

In certain embodiments of the medial anchor 14, the one or more second through apertures 15b includes a single aperture 19 adapted to receive one or more sutures. The aperture 19 can take on various sizes and shapes to facilitate the introduction and traversal of sutures or like members. In other embodiments, the one or more second through apertures 15b includes two distinct and separate apertures 19a, 19b, also capable of taking on various shapes and sizes to accommodate sutures or like members. As disclosed herein, the inclusion of two apertures 19a, 19b can provide better control of suture bending to promote self-locking behavior.

The one or medial anchors 14 of the system 10 can be constructed of various metal or polymer materials including, for instance, PEEK or polypropylene.

Figure 4:
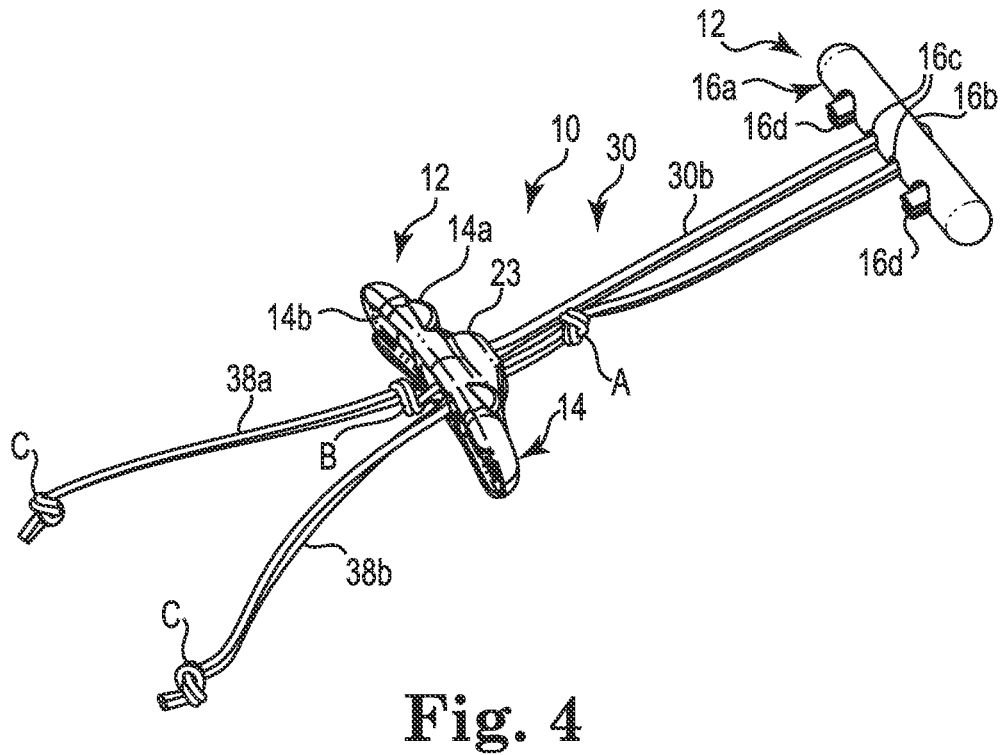
FIGS. 4-5 show an implant device having a distal/lateral anchor, a medial anchor and suture loops, in accordance with embodiments of the present invention.
Figure 5:
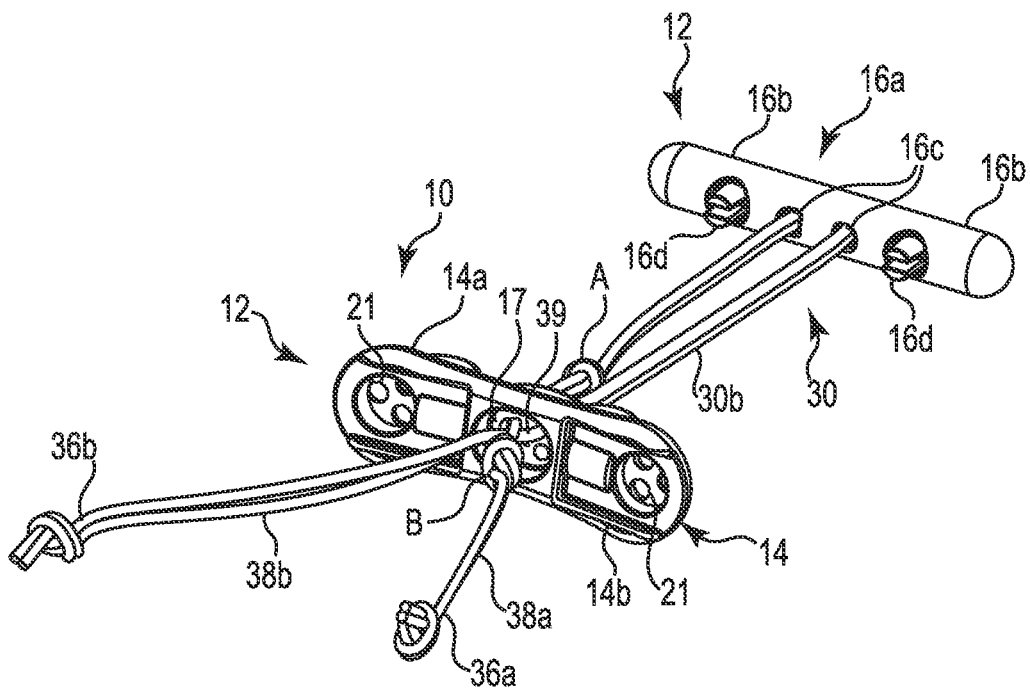
Figure 8:
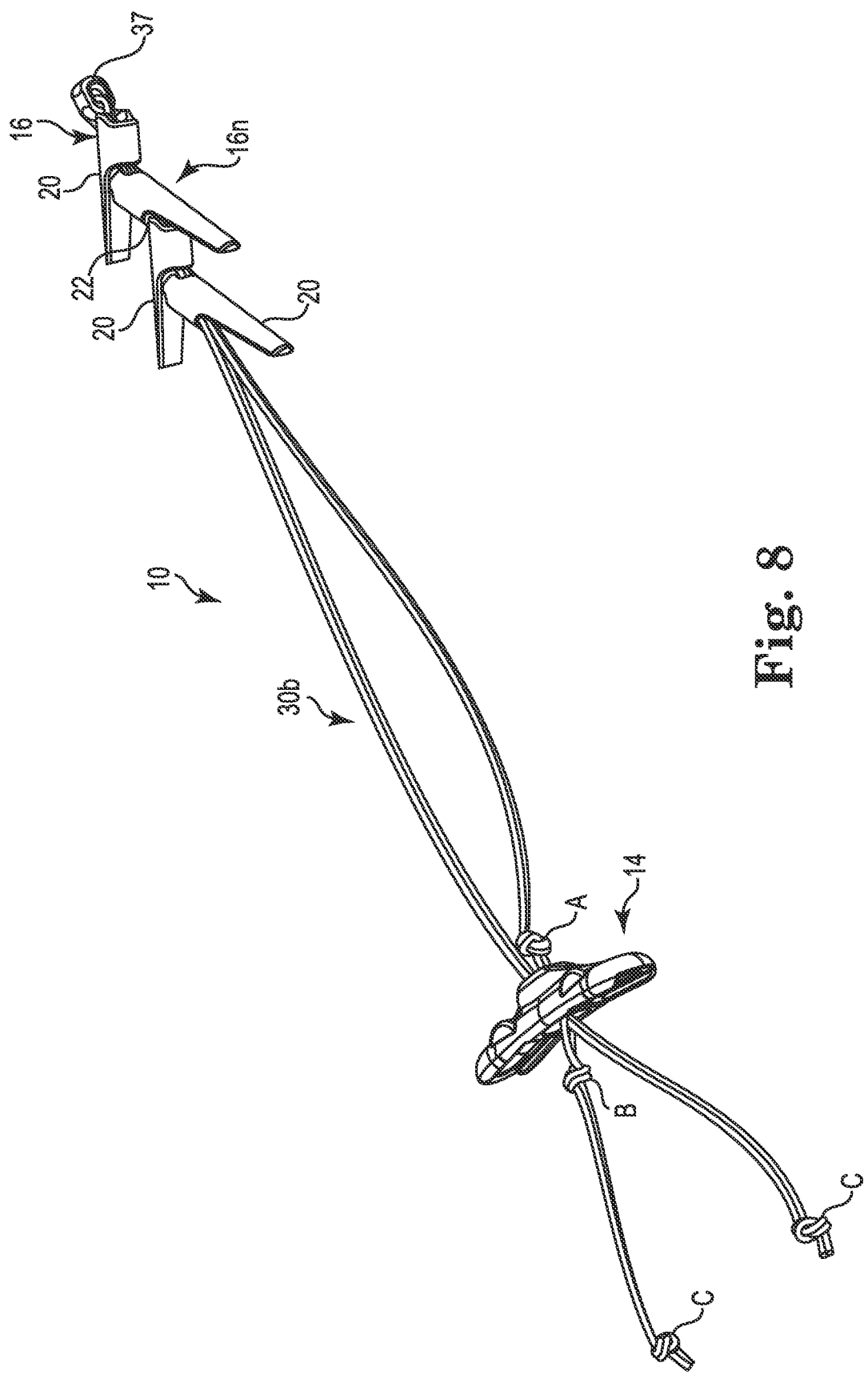
FIG. 8 shows an implant device having an arrayed distal/lateral anchor, a medial anchor and suture loops, in accordance with embodiments of the present invention.
Figure 9:
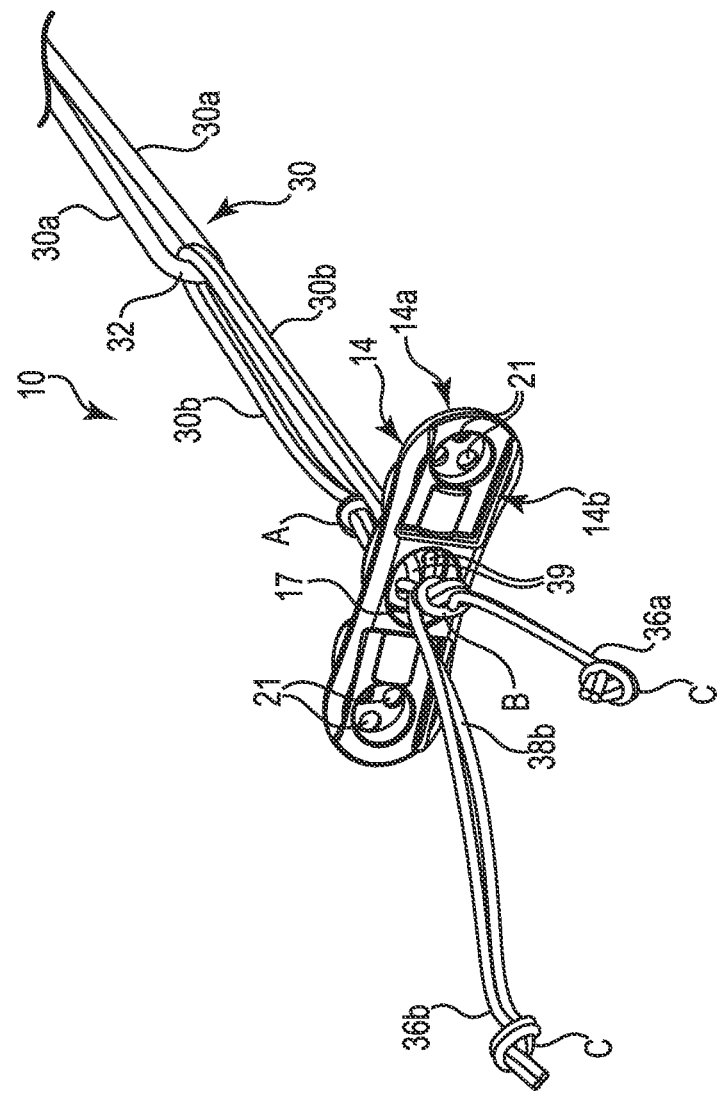
FIGS. 9-10 show partial views of an implant device having a medial anchor, suture loops, and an intermediate pulley mechanism, in accordance with embodiments of the present invention.

FIGS. 4-5 and 8 show an embodiment in which a medial suture loop 30b extends all the way to the anchor 16. With such a construct, the length between the medial anchor 14 and the lateral anchor 16 is entirely available for adjustment. Alternatively, a pulley or pulley surface can be included with the anchor 16 itself (e.g., at the distal end of the implant), eliminating the need for a separate exterior pulley block at a portion of the length of the loop 30b.

Various embodiments of the suture extending through the anchor 16 will include a closed lateral suture loop 30a. The lateral suture loop 30a, in addition to the suture loop 30b, can be provided to extend down from the distal anchor devices 16, as shown in FIGS. 9-18. This loop can be created by providing a monofilament or like suture (e.g., one or more polypropylene 2-0 monofilament sutures) through the distal anchor 16 described herein, with a knot or like stop provided at the distal end of the anchor 16 to close the loop and permit pulling on the loop 30a without causing disengagement of the suture with the anchor or anchor array. As such, the lateral suture loop 30a provides an extended loop or bend portion 32 to facilitate operative connectivity between the anchors 14 and 16. As detailed further herein, the medial anchor 14 can be connected directly with the loop portion 32 via one or more sutures, or the loop portion 32 can include a pulley device 50 to facilitate such connectivity.

In certain embodiments, the lateral suture loop 30a can be created by cutting a length of suture (2-0 suture), bending the suture ends together and then feeding the ends through the respective apertures of the anchor 16. The loop 30a that can range greatly in length and distance from the distal anchor 16, depending on the particular procedure and anatomical needs. In certain embodiments, the length of the loop 30a (measured from the distal end of the anchor 16 to the loop or bend portion 32) can range from 0.5 inches to over an inch. Again, other dimensional characteristics and suture lengths are envisioned for various embodiments of the invention.

The medial suture loop 30b that connects the medial anchor 14 with the distal anchor 16, or the lateral loop 30a, provides tensioning adjustment and selective locking for the implanted device 10, as shown in FIGS. 6-9. In certain embodiments, the medial suture loop 30b is created by cutting, or otherwise providing, a length of suture (e.g., 4-0 suture) having first 36a and second 36b suture ends. The suture 30b length between anchors 14 and 16, as shown in various embodiments (e.g., FIGS. 4-16), is a double stranded suture, or suture pair (e.g., two strands of polypropylene 4-0 suture) and can initially be provided to the physician at a length of approximately 4 inches, and adjusted to approximately 1 to 1.5 inches depending on the tensioning requirements and anatomy of the patient. The end 36b of the suture can be fed through the aperture 15a of the medial anchor 14. Most of the suture length can be fed through the aperture 15a, leaving a short length (e.g., less than 2 inches) and first end 36a on the underside 14b of the anchor 14. A first overhand knot A is tied on the top side 14a of the anchor 14, e.g., approximately 4 inches from the first end 36a of the suture loop 30b.

The suture end 36b can be looped around the bend portion 32 of the lateral suture loop 30a in certain embodiments and brought back down and fed through the at least one aperture 15b of the medial anchor 14. In various embodiments, the at least one aperture 15b includes two spaced apertures 19a, 19b, with a single strand of the paired suture loop 30b passing separately through each one of the spaced apertures 19a, 19b. Other embodiments, such as those depicted in FIGS. 11-14, can include aperture 15a and a single aperture 15b, with both strands of the paired suture loop 30b passing back through the single aperture 15b.

Figure 6:
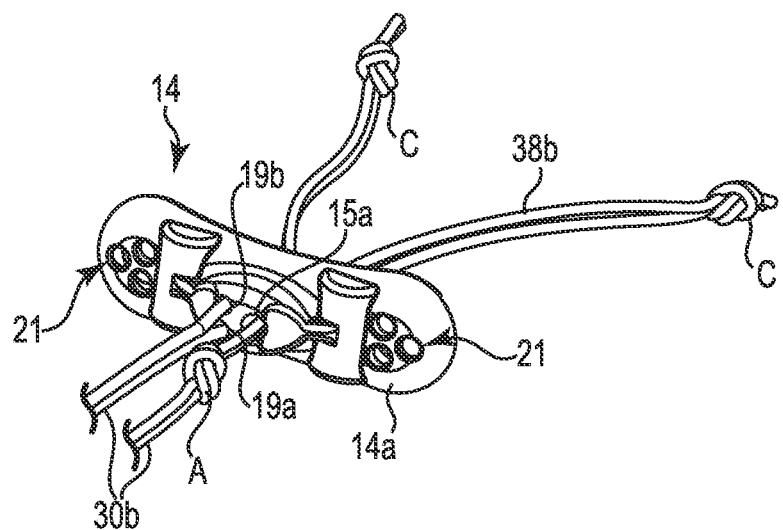
FIGS. 6-7 show a partial view of an implant device, showing a medial anchor device and corresponding suture loop and suture lengths, in accordance with embodiments of the present invention.
Figure 7:
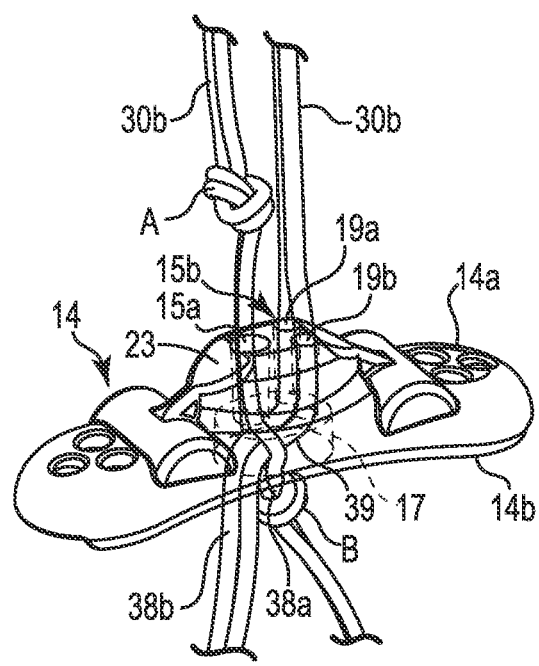

Once through the at least one aperture 15b of the medial anchor 14, the suture end 36b (e.g., including the paired sutures) is passed through and therefore trapped between the paired sutures of the suture 38a extending between the end 36a and the underside 14b of the medial anchor 14, as depicted in FIGS. 6-7. A second overhand knot B is tied on the underside of the medial anchor 14, positioning it close (e.g., approximately 0.02-0.08 inches) to or against the medial anchor 14—with knot A against or a distance from the top side 14*a* of the medial anchor 14. The knots A, B are provided along the same suture length and can be provided relatively close to one another to avoid backlash, yet far enough away to allow free movement of the adjustment end when desired. The functions served by knots A or B can alternatively be provided by other means, e.g., fusing or melting the suture at the same locations, applying a fixed clamping ring, overmolding a bead, et. One or more knots C, or like end or stop features, can be provided at or approximate the ends 36*a*, 36*b* of the suture loop 30*b* that are now provided below the medial anchor 14. The end features can include polymer or like colored tabs (e.g., yellow and blue) provided to assist in identifying the respective suture lengths and grabbing to pull or adjust for loosening and/or tensioning. In other embodiments, one or both of the ends 36*b* can include a loop formed from a reversal of the suture at that point, or an additional closed loop beyond one or both of the knots C or end features. Such a feature can serve as a 'finger loop' and can be used by the physician to make adjustments and to facilitate manual manipulation of the suture lengths.

As shown in FIGS. 4-8, a loosening or lengthening length 38*a* and a cinching or tensioning length 38*b* of suture are provided below the underside 14*b* of the medial anchor 14. By passing the length 38*b* between the pair of sutures of the length 38*a*, the locking mechanism becomes self-locking upon actuation or tensioning between the anchors 14, 16 and requires no additional steps except to trim the suture length upon completion of the procedure. The locking occurs due to cinching from the suture 30*b*, in conjunction with fact that the length 38*b* is forced into a bent configuration, at a relatively sharp angle, to generally prevent sliding or movement of the suture length 38*a*. Those embodiments having two distinct apertures 19*a*, 19*b* (e.g., FIGS. 6-7) can result in sharper bends 39 to the suture passing through them and, consequently, better locking behavior and securement. Namely, each suture of the pair bends directly over its own aperture edge surface to promote locking. Even with little or no tension on the medial anchor 14 or the respective suture portions, the suture does not slip easily or lengthen the loop. Moreover, this arrangement can be easily loosened or tightened by pulling on the appropriate end (e.g., 38*b* for tightening, 38*a* for loosening) and is not generally affected by whether the suture loop has been previously locked down.

As an alternative to knots, other devices, mechanisms or techniques can be employed to facilitate the cinching or locking of the device 10. For example, clamping rings (e.g., swaged rings), adhesive bonds, fusion (melting) of the suture material, or using a specifically designed part that has a split midline (in place of the two sutures between the knots A, B) can be used to facilitate the tensioning or locking features of the present invention.

As described herein, the bend portion 32 of the lateral loop 30*a* can serve as a pulley or pulley surface when engaged with the medial loop 30*b*. Because of the limited amount of movement that may be required during a one-time or limited adjustment of the implant, and the described suture materials, there is not a need for a long lasting bearing surface or separate pulley device/surface in certain embodiments.

Embodiments, such as those shown in FIGS. 10-14, can include the pulley block or device 50. This pulley device 50 can include a first aperture 52 and a second aperture 54, and is provided to connect the lateral suture loop 30*a* with the medial suture loop 30*b*, with at least the medial suture loop 30*b* able to slide freely through the aperture 54 in accordance with the tensioning adjustment described herein.

Figure 10:
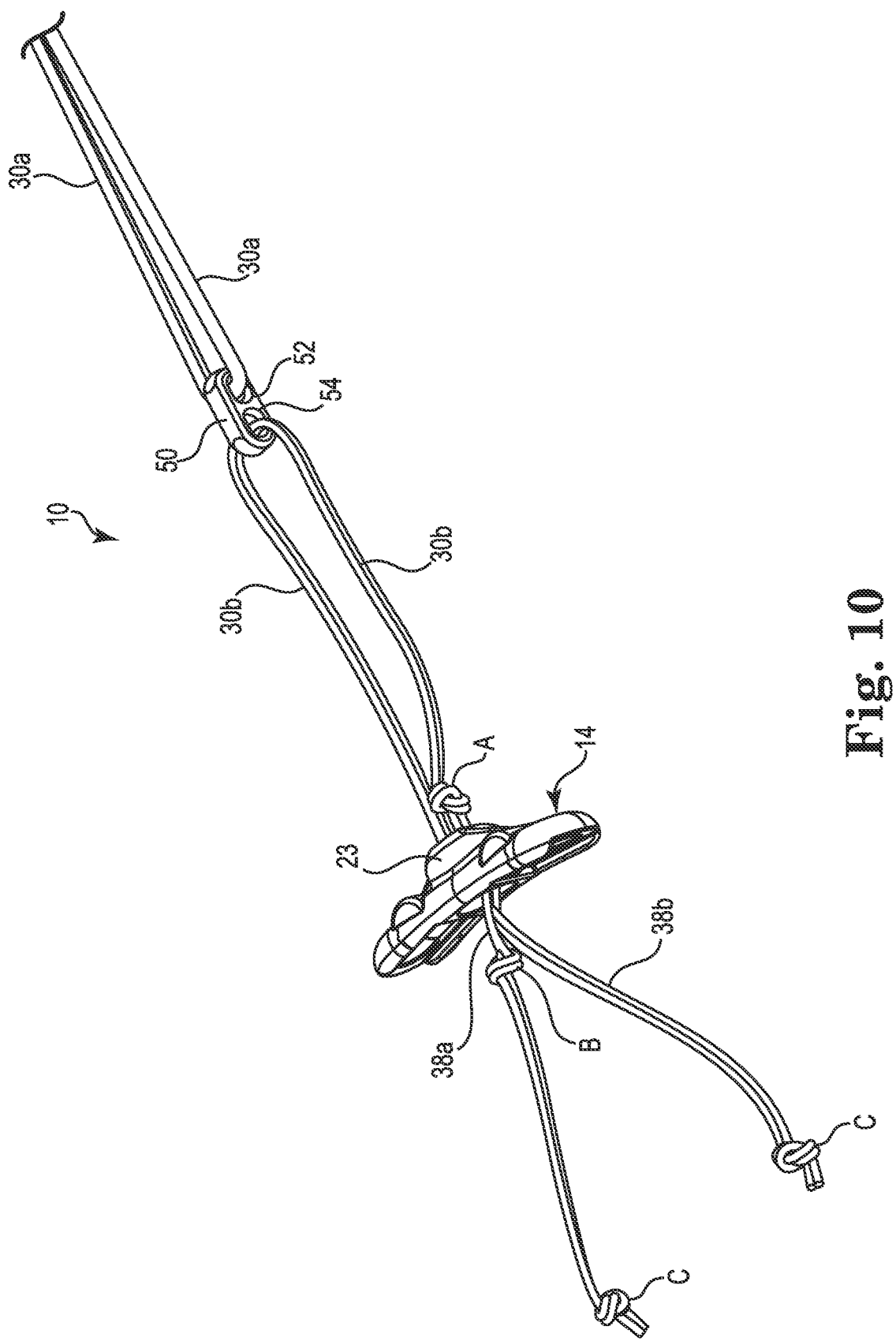
Figure 11:
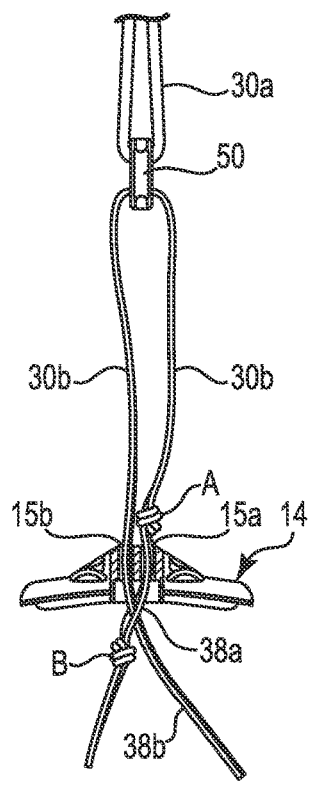
FIGS. 11-13 show partial cross-section schematic views showing an implant device having a medial anchor, suture loops, and an intermediate pulley device, in accordance with embodiments of the present invention.
Figure 12:
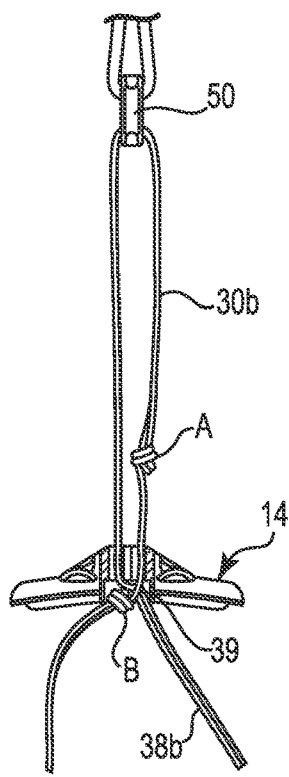
Figure 13:
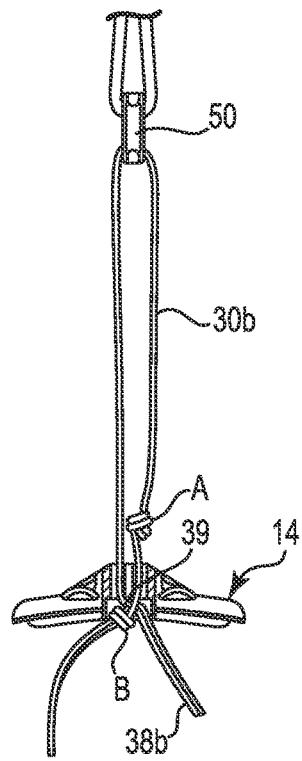

FIGS. 10-11 shows the device 10 and medial anchor 14 in a generally loosened state, with no active force on the components (with or without a pulley 50). The medial suture 30*b* is thus in a slackened state. The medial suture loop 30*b* can resist sliding or spreading even when in this slackened state. This can be attributed to the combination of suture material properties and the dimensions of this design. FIG. 12 shows a tension load being applied between the medial anchor 14 and the pulley 50 (or embodiments with the bend 32), such that the adjustment length is bent at the bend or cinching portion 39 to immobilize the suture loop and movement of the anchor 14. The lock or securement is achieved by both the mechanical binding at the corner bend 39 as well as friction between the sutures and the anchor components.

Figure 14:
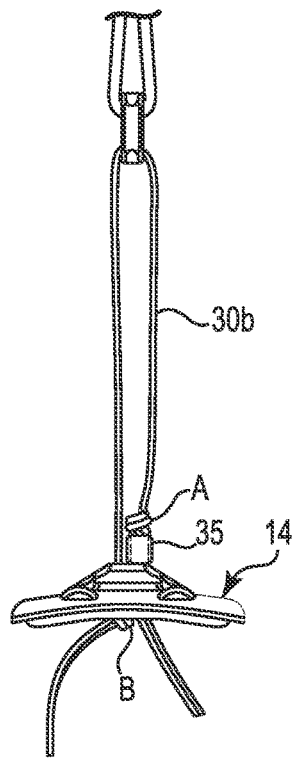
FIG. 14 is partial view of an implant device, showing a medial anchor, suture loops, an intermediate pulley device, and a bushing, in accordance with embodiments of the present invention

FIG. 14 demonstrates an embodiment of the device 10, with or without a pulley 50, having one or more bushing members 35. The bushing member 35 can be an elastic bushing having a through-hole for receiving the length of the suture 30*b* between the knot A and the medial anchor 14. The bushing 35 can reduce the slack of the cinching element such that suture locking is even more immediate, and can also maintain some minimal cinching pressure even if there is no opposing tension between the medial anchor 14 and the pulley 50 or bend 32. Instead of, or in addition to the bushing 35, coil springs, leaf springs, bevel springs, or a spring biasing element can be provided with the medial anchor 14 to achieve this goal. Alternatively, a spring that acts to spread apart the suture pair 30*b* can be employed as well.

Figure 15:
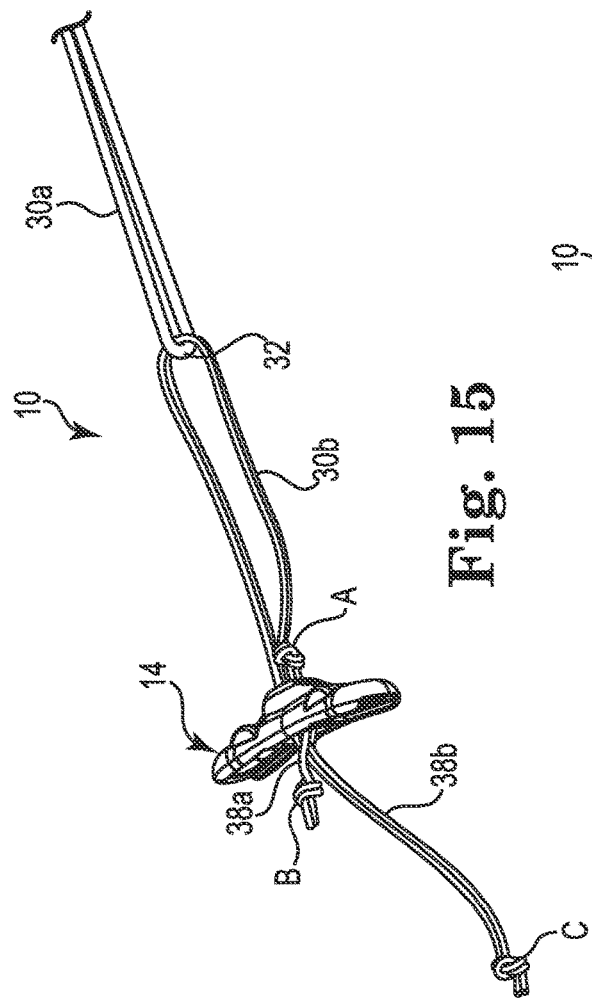

FIG. 15 shows an embodiment of the device 10 having only a single direction of adjustment for the suture locking mechanism. Namely, in some cases it may be desirable to only allow for a single direction of adjustment. This is accomplished by cutting off the trailing portion of the cinching end 38*a*, leaving the suture end 38*b*.

Figure 16:
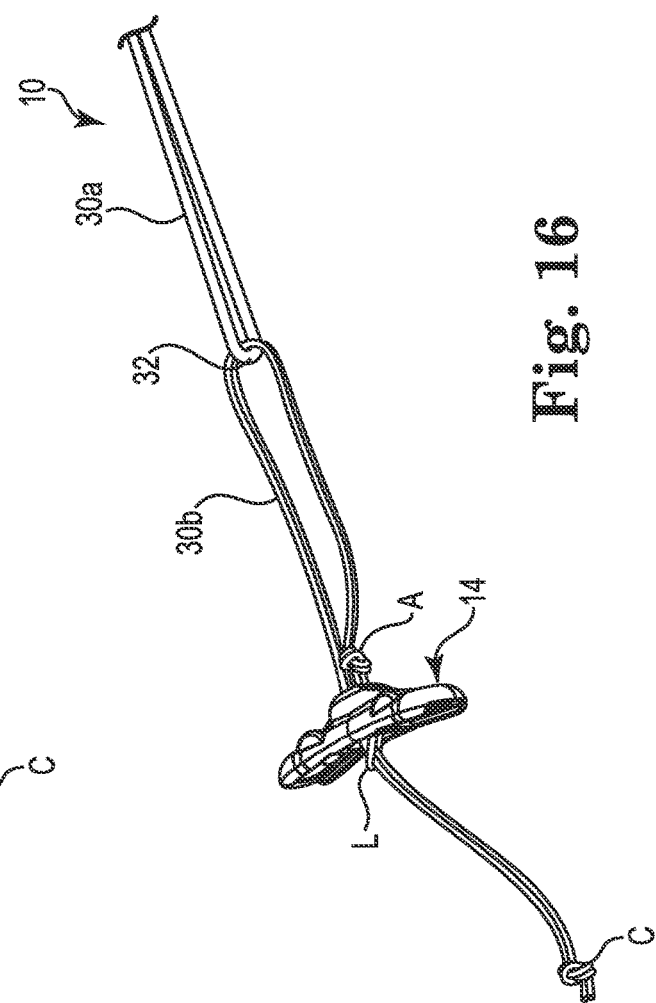

The embodiment of FIG. 16 includes a single-direction adjustment version of the device 10, wherein the knot B is not provided, and a turn-around loop L is instead used to provide the tensioning and cinching adjustment. Length 38*b* passes through the loop L.

FIG. 17 demonstrates an embodiment of the device 10 where the medial loop 30*b* includes a single suture 30, rather than paired sutures. A single suture completes the loop 30*b*, becoming the end 38*b*. Such an embodiment would reduce the amount of material used for the device 10 and could eliminate the potential of paired sutures not being uniformly pulled or cinched during adjustment.

FIG. 18 shows a device having a compound pulley arrangement 33. Namely, the suture length 30*b* between the medial anchor 14 and the bend 32 is looped around twice and then returned through the through-aperture 15*b* of the medial anchor 14 and between the cinching suture pair 38*a*. Such an arrangement can allow a finer adjustment in the shortening direction, and there can be greater cinching pressure bearing down against the single suture (e.g., for a given amount of opposing tension between the pulley surface/device and the medial anchor). However, this embodiment could include a paired suture looping twice above the medial anchor and through the cinching length 38*a* as well.

Figure 19:
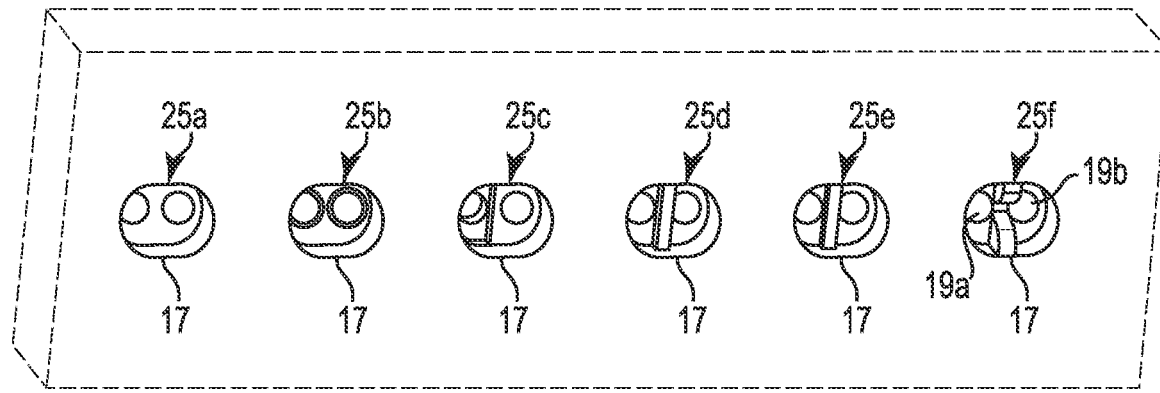
FIGS. 19-21 show schematic views of various medial anchor aperture configurations, in accordance with embodiments of the present invention.
Figure 20:
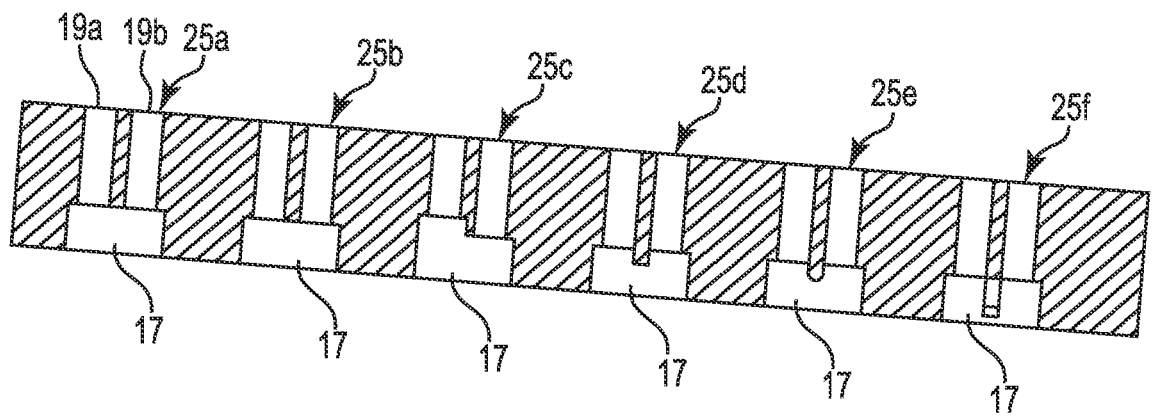

FIGS. 19-20 schematically show various embodiments of the through-apertures 19*a*, 19*b* capable of implementation in the medial anchor 14. For simplicity, the details of the anchor 19 have been omitted, instead focusing on the various possible aperture configurations. The aperture configurations are denoted as 25*a* trough 25*f*. FIG. 19 provides a perspective view of these configurations, while FIG. 20 shows a cross-sectional view.

The apertures 25a, as well as the other embodiments, can be approximately 0.016-0.020 inches in diameter when passing a pair of 4-0 sutures through them. The shape of the pocket 17 can be modified to improve or modify the effectiveness of the cinching element, as shown.

The apertures 25b include edges of the through-holes that have a controlled radius. This can aid in the initial assembly of the suture pair, and can prevent over-compression of the suture or even severing of the suture when under high loads.

With the arrangement of apertures 25c, the pocket 17 includes a step that enhances the bending of the suture end 38b to lock it down. The adjustment suture would pass through the right-most hole.

The apertures of 25d include a ridge between the holes that can improve the locking and cinching of the adjustment suture end. Similarly, apertures 25e can include a rounded-edge ridge to reduce the chances of severing the suture. With apertures 25f, the middle ridge is notched, further increasing the ability to lock the adjustment suture in place.

Figure 21:
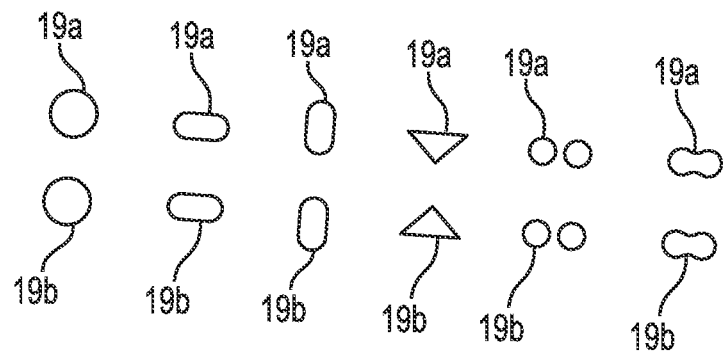
Figure 27:
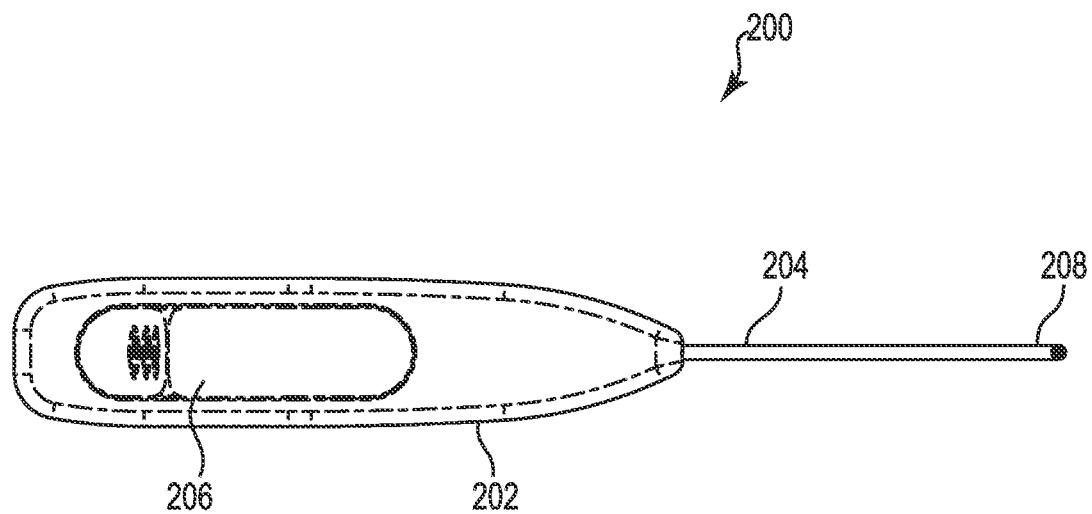
FIGS. 27-28 show a delivery tool device for introducing and deploying an implant, in accordance with embodiments of the present invention.
Figure 28:
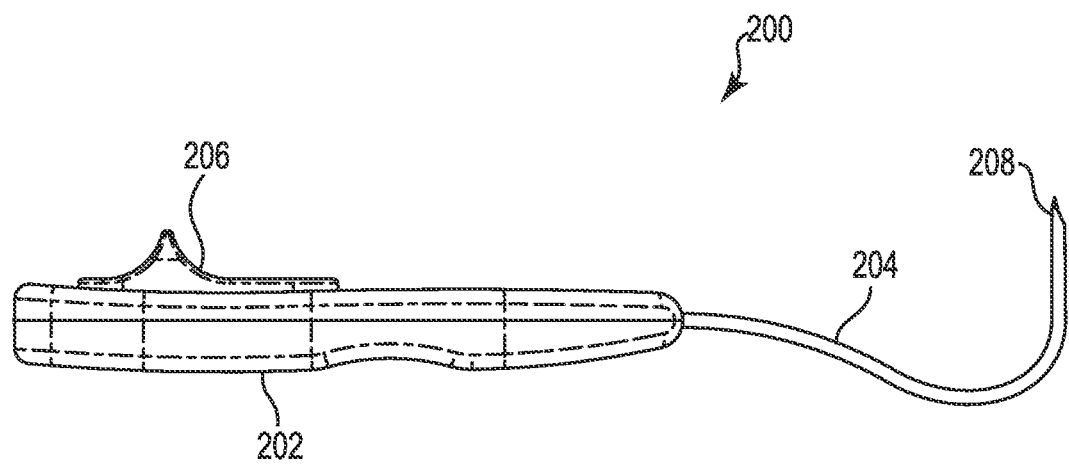
Figure 29:
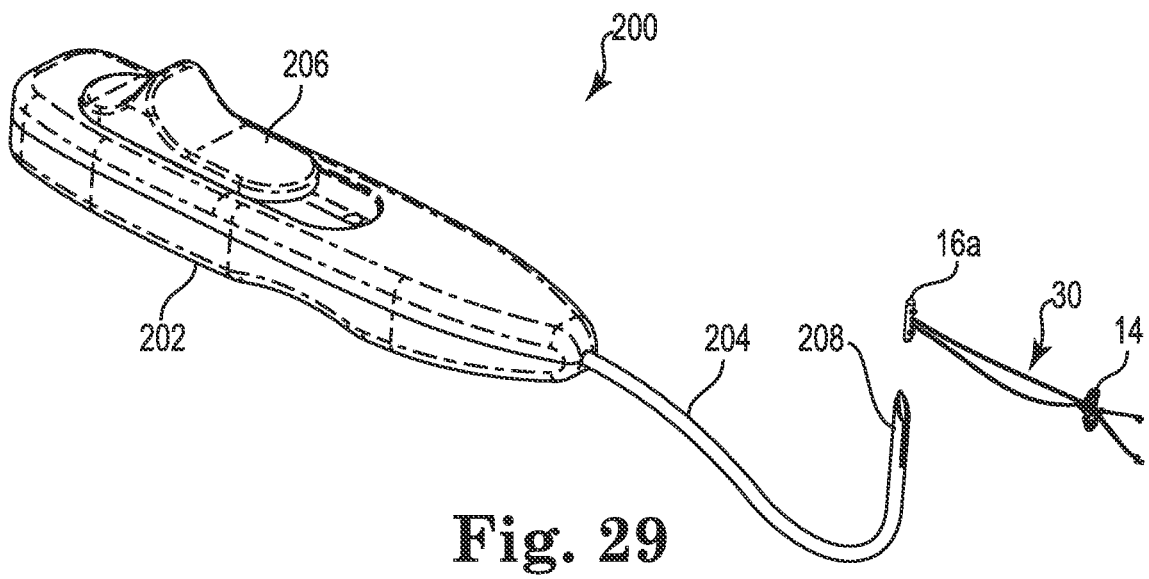
FIGS. 29-30 show a delivery tool device, loading a distal/lateral anchor of an implant, in accordance with embodiments of the present invention.
Figure 30:
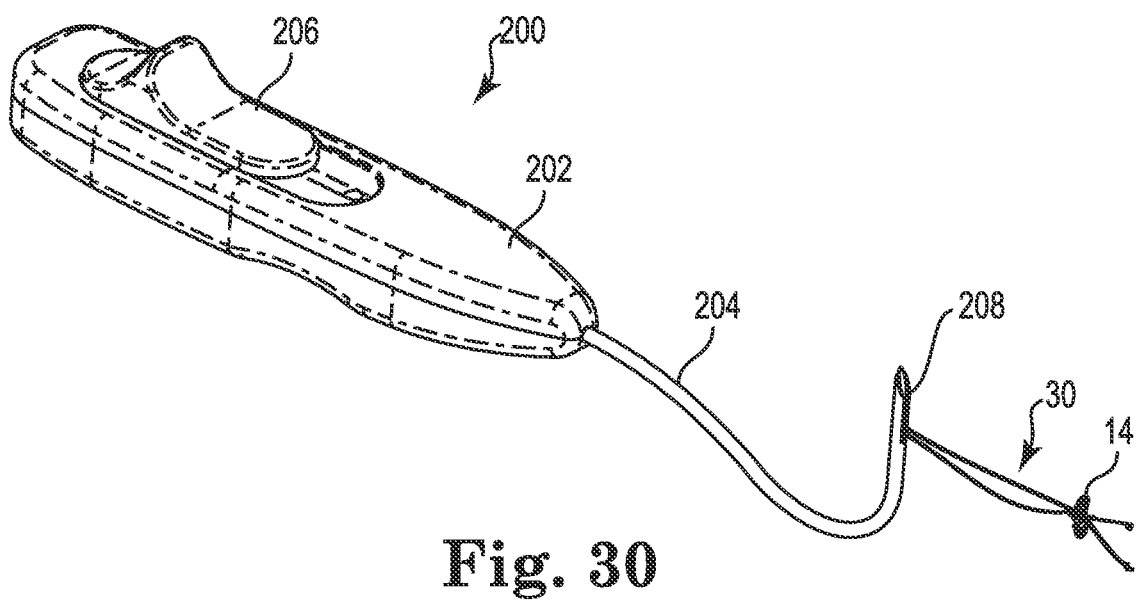
Figure 31:
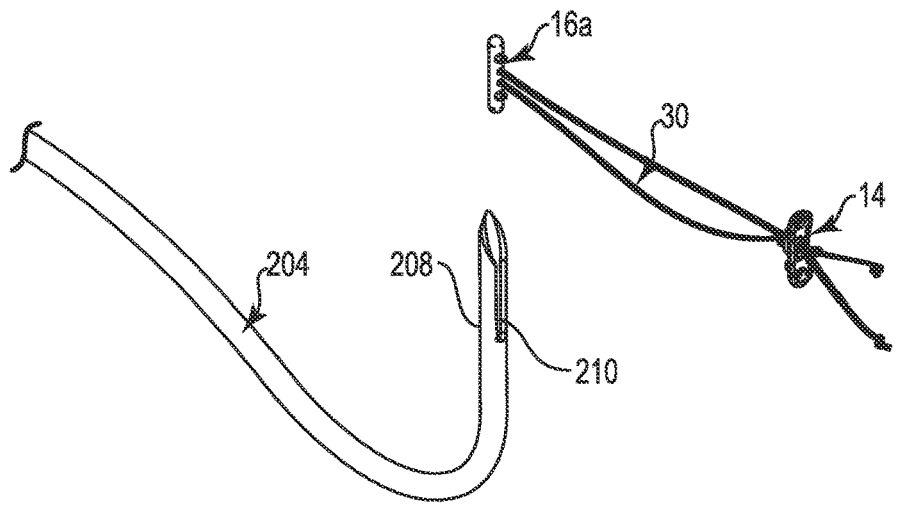
FIGS. 31-32 show partial close up views of a delivery tool device, loading a distal/lateral anchor of an implant, in accordance with embodiments of the present invention.
Figure 32:
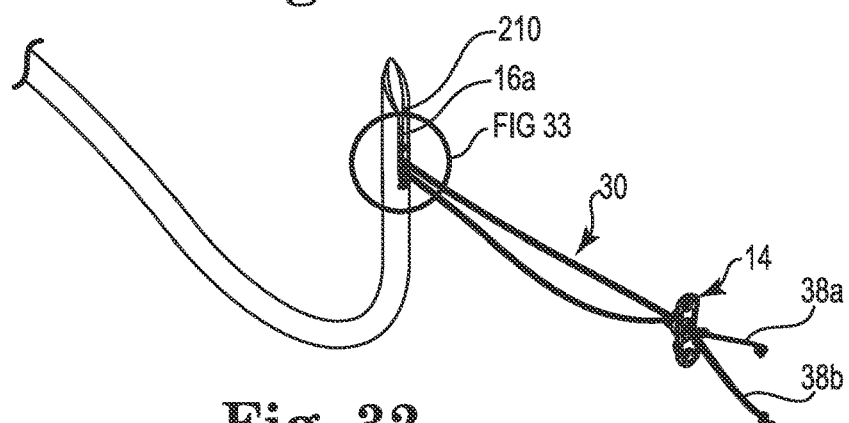
Figure 33:
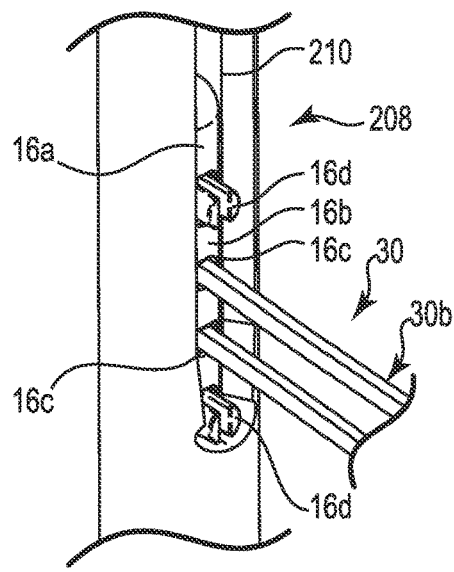
FIG. 33 show a partial close up view of the distal/lateral anchor loaded in the delivery tool device of FIG. 32, in accordance with embodiments of the present invention.

FIG. 21 provides a schematic view of various exemplary shapes and configurations that can define the through-holes 15b, 19a, and/or 19b. Again, different edge surfaces, binding surfaces, and size constraints can serve to better lock the adjustment suture, or suture pair, in place within the medial anchor 14.

Referring again generally to FIGS. 4-5, the lateral anchor device 16 can be a distal toggle anchor 16a having a body portion 16b, one or more loop apertures 16c, and one or more extending members 16d. The toggle anchor 16a is generally elongate and adapted to be carried by a portion of delivery device (e.g., distal needle end) as further detailed herein, for anchoring within soft tissue, e.g., the obturator membrane. The anchor 16a can be constructed of a polymer material, such as PEEK, with the one or more loop apertures 16c configured to receive one or more suture members 30 such that the suture 38b enters a first aperture 16c, loops around a portion of the anchor 16a, and loops back into and through a second aperture 16c for a return path to the medial anchor 14. The one or more extending members 16d are also adapted to be carried within the delivery device, and can facilitate alignment and prevent rotation of the anchor 16a while it is being carried by and deployed from the anchor 16a. Extending members 16d can also be adapted to fit within a slot on the delivery device such that anchor 16a is retained within the delivery device, and to provide stability of anchor 16a within soft tissue—e.g., acting as small barbs to increase its engagement with tissue.

Referring to FIG. 8, various embodiments of the anchor device 16 can include a body portion having one or more expandable barbs 20, and a thru-aperture 22. A suture, such as a suture loop 30b or 30a, or like member, is adapted to string or thread through the respective apertures 22 of a series or array 16n of such anchors to define the general elongate and expandable configuration shown. Embodiments of the lateral anchors 16 can include self-expanding structures or materials such that the anchors 16, or anchor array 16n, can be generally collapsed or reduced in sized during deployment, with or without a needle device, and expanded after penetration in the target tissue site to provide desired tissue engagement. Certain anchors 16 can include one or more shape memory portions, or living hinges, to facilitate this structural self-expansion upon deployment and tissue engagement. The implant, anchoring and deployment devices, components, tools, techniques and methods disclosed in U.S. Patent Publication Nos. 2013/0023724 and can be employed with, in whole or in part, embodiments of the present invention and, as a result, this patent publication is hereby incorporated fully herein by reference. The array of anchors 16n can be inserted within and along the interior lumen of a needle, cannula or like inserter or delivery tool.

In various embodiments, the lateral anchor devices 16 can be directed for engagement with tissue distal the anchors 14 at target sites such as the obturator membrane, obturator internus muscle, sacrospinous ligament, prepubic fascia or muscle, abdominal fascia, rectus fascia, puboprostatic ligament, the tendinous arch of the levator ani, the Cooper's ligament, and the pubic symphysis. Other distal target tissue sites for the anchors 16 capable of permitting tensioning support for the perineal membrane or other urethra-supporting tissue is envisioned as well. In addition, other tissue, muscle or ligaments associated with orthopedic, plastic surgery or similar procedures can be targeted for fixation, adjustment and tensioning using the devices 10 and systems disclosed herein.

Unlike conventional pelvic sling devices and implantation methods, the path from the perineal membrane to the distal anchor 16 of the present invention can follow a generally straight line into the obturator internus muscle, or like distal tissue. Furthermore, because it intersects the muscle at an oblique angle, more tissue can be engaged for securement.

In certain embodiments, the various anchors can be fabricated using a metal injection molding process, or from a molded resin material (e.g., polypropylene, polycarbonate, PEEK, nylon), with an exemplary Polypropylene monofilament, or braided, suture, or suture loop 30a, threaded therethrough.

The systems, devices, configurations and methods disclosed herein have generally described anchors that are symmetrically, bilaterally, positioned above, below or on the side of the urethra. However, a single side deployment configuration can still achieve continence and is available with various embodiments. For instance, a single medial anchor 14 and lateral anchor 16, or lateral anchor array 16n, can be connected by one or more sutures to support and adjust the perineal membrane, above, below, or on a side of the urethra.

Various embodiments of the implant 10 can include a pulley tensioning device 100, as shown in FIGS. 22-26. In this embodiment of the implantable device 10, the adjustment means for increasing tension (decreasing distance) between the distal anchor 16 in the obturator and the medial anchor 14 at the perineal membrane includes the intermediate pulley-like mechanism 100. This mechanism 100 is fixedly attached to the distal anchors 16 via the suture 30. A second suture 50 is connected to the medial anchor 14 and passes through a pulley carrier 102 and reverses direction about a bearing surface 104. The suture 50 continues through one-way barbs or like members or structures 106 that allow movement of the suture 50 in only a single direction. The second suture 50 can be braided to enable effective stoppage against the barbs 106 in the suture stopper 108. The distal anchor 16 and pulley mechanism 100 can be sized to fit within the same delivery needle systems described herein. By separating the tensioning mechanism 100, the medial anchor 14 can be smaller, enabling easier placement through a small needle puncture. Another advantage of this embodiment can be that the process of adjusting tension is simple and a one-way movement embodiment where that is desirable. The user or physician only needs to pull on the tensioning end of the suture 50.

Referring to FIGS. 27-35, embodiments of the present invention can include one or more delivery tools or devices

200. The tool 200 can include a handle portion 202, a needle portion 204, and an actuator mechanism, switch or button 206. The needle portion 204 can be curved or straight, and can include a distal end portion 208. The needle portion 204 can include a lumen and the distal end portion 208 can be slotted at slot 210.

The slot 210 at the distal end portion 208 is sized and shaped to slidably and selectively receive and secure the anchor 16, including anchor 16*a,* therein. An end portion of the slot 210 can be narrowed or tapered to help retain the anchor 16*a* within the needle. Upon introduction through the target tissue location (e.g., obturator membrane), the mechanism 206 can be actuated (pushed, pulled, slid, etc.) to release the anchor 16 from the distal end portion 208. A wire, rod or like member within the lumen of the needle portion 204, and operatively connected to the mechanism 206, can therefore traverse to push or otherwise release the anchor 16 from the distal end portion 208. Again, the extending members 16*d* of the anchor 16*a* can be included to facilitate slot alignment and loading of the anchor along the slot 210 of the distal end portion 208 and to generally resist rotation of the anchor during deployment.

Figure 34:
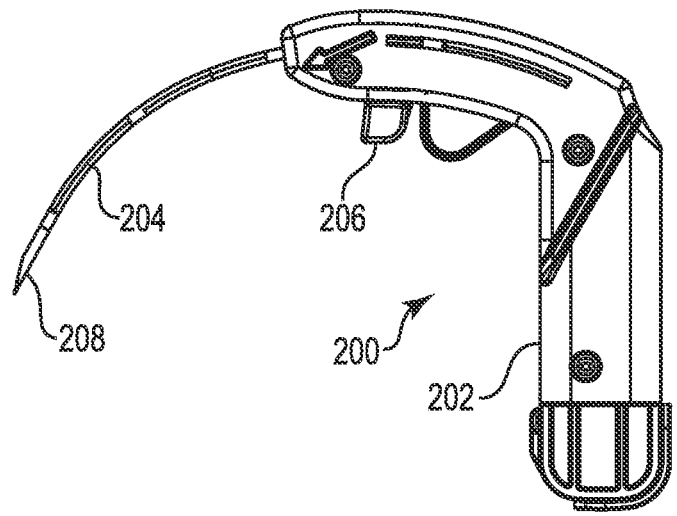
FIGS. 34-35 show a delivery tool device for introducing and deploying an implant, in accordance with embodiments of the present invention.
Figure 35:
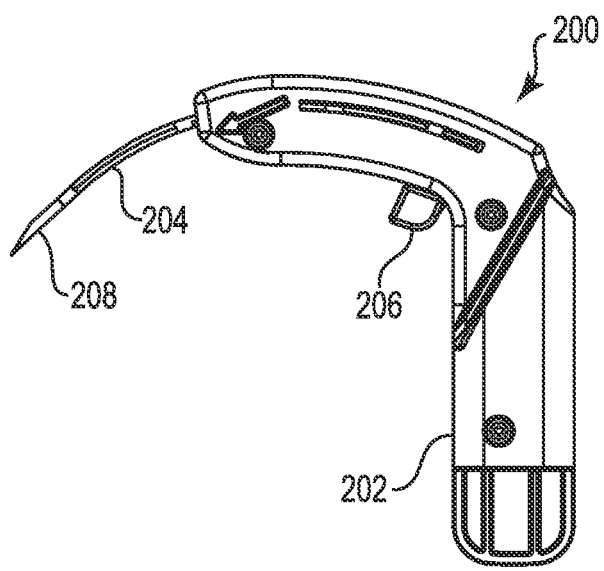

The embodiment of the tool 200 in FIGS. 34-35 can also receive and deploy the anchor 16, with the mechanism 206 adapted to slide back and correspondingly retract the needle portion 204 into the handle 202. Markings on the needle portion 204 can provide indicia of tissue depth to assist the physician in deployment of the implant.

One embodiment of deploying and implanting the implant 10 of the present invention to treat a female pelvic disorder includes first prepping the patient by positioning her legs generally in a dorsal lithotomy position. A target location for each lateral anchor on the externus side of the obturator membrane, at the superior medial notch of the obturator foramen. Next, the physician locates the superior medial notches of the obturator foramina for visual guidance and can accordingly mark, on each side, with a pen, palpating to confirm positions. A foley catheter can be used to drain the bladder, with the catheter left in place after clamping.

Skin puncture sites are lateral to the urethral meatus or opening, in the vertical sulci or creases approximately 2-5 mm from the lateral margins of the catheter (3 and 9 o'clock locations). A local anesthesia can be delivered to the anterior wall of the distal vagina near the puncture site and from the puncture site to a depth of approximately 20 mm, moving parallel to the urethra. 5 to 10 mm Allis or Babcock forceps can be attached to the distal anterior vaginal wall just below the puncture site.

Then, the physician can locate the puncture site for the delivery tool by evenly spreading the labia minora. The puncture site can lie along the vertical crease or sulcus between the urethral meatus and the labia, 2-5 mm from the lateral margin of the catheter. The punctures can be at the 3 and 9 o'clock position on this crease. While evenly spreading the labia minora, the physician can use a scalpel to create a shallow (approximately 5 mm deep), vertical stab incision through the skin and Colles' fascia at the puncture site.

Next, the implants 10 and the delivery tool 200 are provided. The lateral anchor 16 is attached to the needle tip 208 by sliding it into the slot 210 until a click or like response is detected. The labia minora can be spread, inserting the delivery tool needle 204 superficially into the stab incision. The delivery tool handle 202 may be pointed upward to minimize interference.

The needle tip 208 can then be advanced through the perineal membrane, along a direction parallel with, or slightly diverted from, the urethra. The penetration depth is approximately 20 mm, or roughly the straight length of the needle tip 208 before the curvature starts. Next, the handle 202 can be pivoted about the needle tip 208, aligning it with the target mark. Then the needle tip 208 can be pulled laterally toward the mark until the side of the needle pushes against the inferior ramus bone. With the needle tip 208 aligned to the mark, the handle 202 is rotated until the needle tip is generally perpendicular to the obturator foramen. The curved portion of the needle 204 can be pushed to drive the tip 208 in a straight line through the obturator membrane, stopping after puncturing.

Holding the delivery tool 200 stationary, the physician will push the slider or like mechanism completely forward to release the anchor 16, then letting the internal spring return the slider. The physician can then ensure the sutures are completely free from the delivery tool 200 and initially retract the needle in a straight line out of the obturator muscle.

Pulling on a tabs or suture ends 36*a,* 36*b* will confirm movement of the medial anchor 14. Pulling the a tab or suture end 36*a* should move the medial anchor 14 away from the patient or anchor 16, lengthening the space between the anchors 14, 16. Pulling a second tab or suture end 36*b* should move the medial anchor 14 toward the patient, shortening the distance between the anchors 14, 16. Generally, pulling on the second tab should stop when the medial anchor 14 is near the puncture site.

Next, the physician can hold the medial anchor 14 parallel to the urethra in order to insert it through the skin puncture. A hemostat can be oriented with the external sutures upward. The medial anchor 14 continues to be inserted until the clamped, distal end is about 5 mm below skin level, ensuring that the anchor 14 is buried, with continual pulling on the suture 36*b* with the second tab to take up any slack. When the medial anchor 14 is ready to be released, the proximal end of the anchor is tipped anteriorly. If a correction is required, the anchor 14 may be fully retrieved by pulling on the tab or the suture line 36*a* and reinserting with a hemostat or like device.

The physician can continue to pull on the second tab (e.g., blue) or end 36*b* to set the medial anchor 14 against the perineal membrane. This position is noted when the tissue around the puncture pulls inward or dimples. This second tab (e.g., blue), provided with suture length 38*a,* can be pulled to increase (loosen) the spacing between the anchors 14, 16 if excessive tension is noted (by strong movement of tissue).

These surgical procedures steps, devices and techniques are repeated contralaterally, on the other side of the urethra. A surgeon's knot can be created with the suture of the two tabs or ends, and pushed below the skin level. While pushing the knot, each suture end can be pulled uniformly to minimize further anchor spacing adjustment. The skin layer is then pulled up to conceal the implant and suture ends and each skin puncture is closed with absorbable or like sutures, or topical adhesive.

The systems, their various components, structures, features, materials and methods of the present invention may have a number of suitable configurations as shown above. Various methods and tools for introducing, deploying, anchoring and manipulating implants or to treat incontinence and prolapse as disclosed in the previously-incorporated references are envisioned for use with the present invention as well.

A variety of materials may be used to form portions or components of the implants and devices, including Nitinol, polymers, elastomers, porous mesh, thermoplastic elastomers, metals, ceramics, springs, wires, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A surgical implant system, comprising:
  a delivery device having a distal end portion including a sidewall defining a slot;
  an implant device having a medial anchor, a lateral anchor, and a suture operatively connecting and extending between the medial anchor and the lateral anchor, the lateral anchor including a body portion, a first aperture extending in a first direction, and a second aperture, the lateral anchor including a first extending member having an end and a second extending member having an end, the first aperture being disposed between the second aperture and the first extending member, the second aperture being disposed between the first aperture and the second extending member, a portion of the first extending member and a portion of the second extending member being configured to fit within the delivery device to facilitate alignment, each extending member is configured to extend from the slot of the delivery device in a direction substantially parallel to the first direction, a first portion of the suture being configured to extend through the first aperture, out from the slot of the delivery device, and to a location between the end of the first extending member and the end of the second extending member, a second portion of the suture being configured to extend through the second aperture, out from the slot of the delivery device, and to a location between the end of the first extending member and the end of the second extending member, and a third portion of the suture extending between the first portion of the suture and the second portion of the suture, the third portion in its entirety being configured to be disposed within the delivery device, at least a portion of the third portion of the suture being configured to be disposed within the delivery device adjacent the sidewall of the delivery device such that the at least a portion of the third portion of the suture is disposed between the sidewall of the delivery device and the lateral anchor, the suture including a knot, the medial anchor being disposed between the lateral anchor and the knot,
  the suture extending through to facilitate selective locking adjustment of the medial anchor in position upon deployment.

2. The system of claim 1, wherein the medial anchor includes a third aperture.

3. The system of claim 1, wherein the suture forms a lateral suture loop and the at least a portion of the third portion of the suture is configured to be disposed within the delivery device directly adjacent the sidewall of the delivery device such that the at least a portion of the third portion of the suture is disposed directly between the sidewall of the delivery device and the lateral anchor.

4. The system of claim 1, wherein the suture includes a tensioning suture length and an adjustment suture length extending out from a bottom surface of the medial anchor.

5. The system of claim 4, wherein the adjustment suture length passes through and is trapped within the tensioning suture length.

6. The system of claim 5, wherein the tensioning suture length includes the knot, the knot being disposed proximate the bottom surface of the medial anchor.

7. The system of claim 1, wherein the medial anchor is adapted for engagement with a perineal membrane.

8. The system of claim 1, wherein the lateral anchor is adapted for engagement with an obturator foramen.

9. The system of claim 1, wherein the suture has a first terminal end and a second terminal end.

10. The system of claim 1, wherein the body portion of the lateral anchor includes a first end portion and a second end portion, the first extending member is disposed between the first end portion and the first aperture, the second extending member is disposed between the second end portion and the second aperture.

11. The system of claim 1, wherein the knot is a first knot, the suture including a second knot, the second knot being disposed between the medial anchor and the lateral anchor.

12. The system of claim 1, wherein the first extending member, the first aperture, the second aperture, and the second extending member are aligned.

13. A surgical implant system, comprising:
  an implant device having a medial anchor, a distal anchor, and at least one suture operatively connecting the medial anchor and the distal anchor, the at least one suture includes an elastomeric material and extends between the medial anchor and the distal anchor, the distal anchor including a body portion, a first aperture, and a second aperture such that a suture portion of the at least one suture extends through the first aperture, extends through the second aperture towards the medial anchor, and extends to a location between an end of a first extending member of the distal anchor and an end of a second extending member of the distal anchor, the first aperture being disposed between the second aperture and the first extending member, the second aperture being disposed between the first aperture and the second extending member, the first extending member having a first portion and a second portion defining a space devoid of material between the first portion and the second portion,
  the medial anchor includes a first surface portion and a second surface portion opposite the first surface portion, the first surface portion including a raised portion extending from the first surface portion to at least partially cover a knot of the at least one suture,
  the at least one suture extending through one or more apertures of the medial anchor to facilitate selective locking adjustment of the medial anchor in position upon deployment, a portion of the suture extending from the one or more apertures and being disposed between the end of the first extending member and the end of the second extending member; and
  a delivery tool having a handle portion and a needle portion, the needle portion being configured to move with respect to the handle portion such that a first portion of the needle portion is disposed within the handle portion in a first configuration and the first portion of the needle portion is disposed outside of the handle portion in a second configuration, the delivery tool being adapted to receive the extending member of the distal anchor and at least a portion of the suture such that the at least a portion of the suture is disposed within a slot defined by the needle portion of the delivery tool and such that the distal anchor is disposed between the at least a portion of the suture that is disposed within the slot and an opening of the slot, at least a portion of the suture being configured to be disposed within the delivery device adjacent a sidewall of the delivery device such that the at least a portion of the suture is disposed between the sidewall of the delivery device and the distal anchor.

14. The system of claim 13, wherein the at least one suture includes a medial suture loop including a suture pair having first and second suture members.

15. The system of claim 14, wherein the one or more apertures in the medial anchor includes a first aperture to receive the suture.

16. The system of claim 15, wherein the medial anchor includes a third aperture.

17. The system of claim 13, wherein the at least one suture includes a distal suture loop and a medial suture loop.

18. The system of claim 13, wherein the at least one suture includes a tensioning suture length and an adjustment suture length extending out from a bottom surface of the medial anchor.

19. The system of claim 18, wherein the adjustment suture length passes through and is trapped within the tensioning suture length.

20. The system of claim 13, wherein the first extending member, the first aperture, the second aperture, and the second extending member are aligned.

* * * * *